Figure 4:
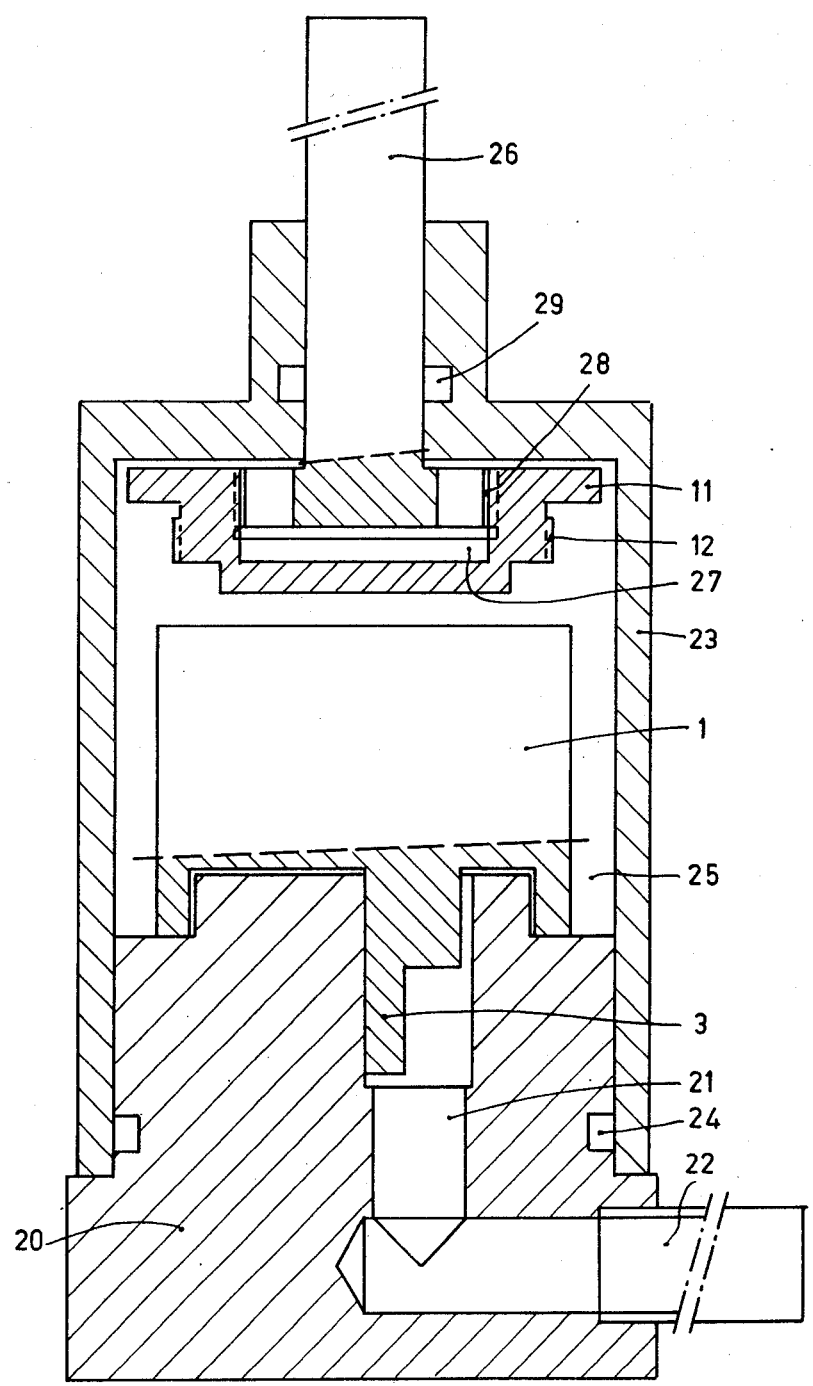

United States Patent [19]

Kessels

[11] 3,973,120
[45] Aug. 3, 1976

[54] SPECIMEN HOLDER FOR AN X-RAY DIFFRACTION APPARATUS

[75] Inventor: Henricus Mathias Marie Kessels, Eindhoven, Netherlands

[73] Assignee: U.S. Philips Corporation, New York, N.Y.

[22] Filed: Feb. 27, 1975

[21] Appl. No.: 553,746

[30] Foreign Application Priority Data

Mar. 7, 1974 Netherlands .................... 7403065

[52] U.S. Cl. ........................ 250/272; 250/277 CH
[51] Int. Cl.² ........................................ H01J 37/20
[58] Field of Search ........... 250/272, 273, 274, 275, 250/276, 277, 278, 279, 439, 451, 456

[56] References Cited
UNITED STATES PATENTS 3,051,834   8/1962   Shimula ............................ 250/277

*Primary Examiner*—Craig E. Church
*Attorney, Agent, or Firm*—Frank R. Trifari; Leon Nigohosian

[57] ABSTRACT

A specimen holder comprising a specimen space to be conditioned for an X-ray diffraction apparatus which is provided with a radiation window which is made of beryllium and which closes an opening in the holder over an arc of 180° in a vacuumtight manner. To this end, the window is annealed to a temperature of approximately 600°C. The specimen is provided on a removable support table, a support face of which contains the axis of curvature of the window.

5 Claims, 4 Drawing Figures

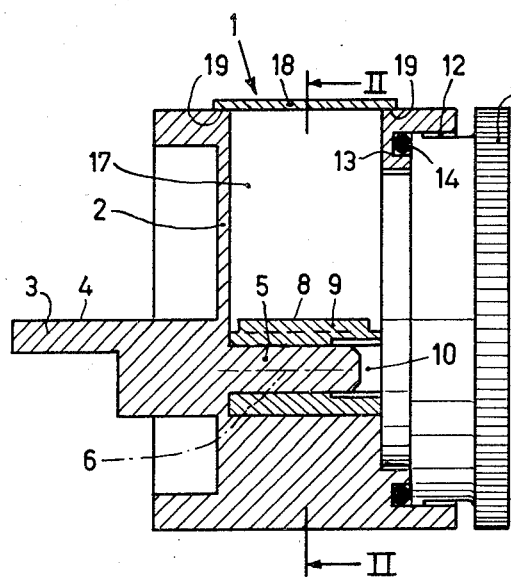
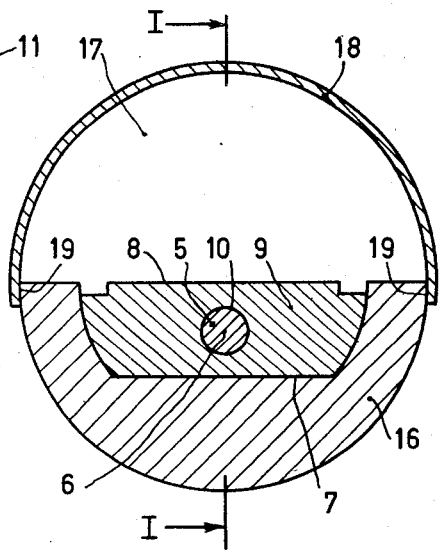
Fig. 1   Fig. 2
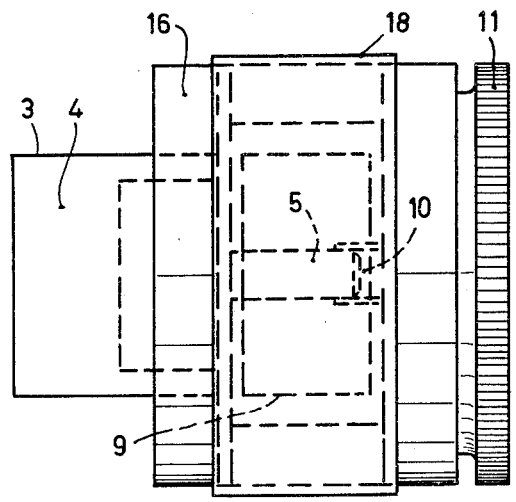
Fig. 3

SPECIMEN HOLDER FOR AN X-RAY DIFFRACTION APPARATUS

The invention relates to a specimen holder for a specimen which is to be fixed in a space to be conditioned so as to be analyzed in an X-ray diffraction apparatus.

In X-ray diffraction apparatus use is often made of specimen holders in which the specimen is exposed to the ambient atmosphere during the examination. For specimens requiring a conditioned specimen space, for example, evacuated or filled with an inert gas, the operator must take special steps which usually are either inadequate or lead to an excessively large and unmanageable specimen holder. Usually adaptation of the goniometer or the shielding of the X-ray diffraction apparatus is also required. For example, it is known to cover the specimen with a layer of a resistive material. However, the accuracy of the analysis can be adversely affected thereby. It is also known to construct a specimen holder which is provided with a vacuum valve. However, a provision of this kind makes the holder heavy and unmanageable. Notably the additional weight of such a specimen holder can give rise to less reliable measuring data.

The invention has for its object to provide a specimen holder in which ease of positioning of the specimen in the diffraction apparatus is maintained and a closed specimen space is realized without the specimen holder becoming less manageable or giving rise to less accurate measuring results.

A specimen holder of the kind set forth according to the invention is characterized in that the holder comprises a housing which can be closed vacuumtight and which is provided with an external abutment face the speciment which is to be arranged on a removable support table occupying a fixed position with respect to the said abutment face and with a radiation window which is preferably made of beryllium and which extends at least over a portion of a cylinder jacket about the specimen table.

Because in the specimen holder according to the invention the specimen is arranged in a space which is to be evacuated and which is closed also by the curved beryllium window, the atmosphere about the specimen can be chosen at random without the specimen holder becoming less manageable. Due to the coupled fixing device, the position of the specimen is unambiguously fixed after insertion into the diffraction apparatus. The specimen holder can have such a simple construction that it can be freely exchanged with the specimen holders supplied with the diffraction apparatus. The invention also relates to a device for conditioning the specimen space after a specimen has been inserted. Because the specimen holder according to the invention is suitably vacuumtight, the conditioning can be performed, if desired, quite some time before the actual measurement commences.

Preferred embodiments according to the invention will be described hereinafter with reference to the drawing.

FIG. 1 is a diagrammatic sectional view of a specimen holder according to the invention, FIG. 2 is a sectional view of the specimen holder taken along the line II—II in FIG. 1, FIG. 3 is a plan view of the specimen holder according to FIG. 1, and FIG. 4 is a diagrammatic representation of a device for conditioning the specimen space in a specimen holder according to the invention.

A preferred embodiment of a specimen holder as shown in FIG. 1 comprises a housing 1, for example, in the form of a hollow cylinder having a closed end face 2 on which an external flange 3 having an abutment face 4 is provided. In the housing 1 there is provided a fixing device, in this case formed by a pin 5, the axis 6 of which extends parallel to the abutment face 4. An abutment face 7 for the positioning can also be provided inside the housing. Suitable orientation and clamping are realized in the preferred embodiment shown in the drawing by providing an abutment face 7 as well as a fixing pin 5. It is to be noted that the axis 6 of the pin 5 need not necessarily coincide with an axis of rotation of the housing. Coincidence is even not to be preferred because it is advantageous to have a support face 8 of a support table 9, to be arranged about the pin 5 so as to be removable via a boring 10, through the axis of rotation of the housing. The position of the specimen in the specimen holder is thus completely fixed by the internal fixing device. The housing can be closed by a lid 11 which is provided, for example, with a thread 12, but which may also be connected to the housing by way of a clamping device. So as to ensure airtight sealing, the cylinder is provided with a recess 13 in which an 0-ring 14 can be accommodated. Contrary to many known specimen holders containing a space to be conditioned, the 0-ring need not be slid along a surface of the specimen holder when a specimen is exchanged. If desired, even the residual friction between the 0-ring and the lid can be eliminated, for example, by choosing a lid which need not be turned so as to be closed.

In a preferred embodiment the support table 9 is provided with a coupling mechanism, for example, a coarse thread 15 in one end of the boring 10, so that the support table can be exchanged by means of a key. All operations to be performed on the specimen holder for exchanging a specimen are preferably such that they can be readily performed in a glove box.

In the cylindrical wall 16 of the specimen holder there is provided a radial slot 17 which extends preferably over at least 180° and which has a width of, for example, 10 to 15 mm in the axial direction of the housing. The slot 17 is covered by a window 18 which is comparatively readily transparent to the X-radiation to be used and which can bear at least a pressure of one atmosphere to permit evacuation of the specimen space. In the described preferred embodiment according to the invention, the window is made of beryllium for this purpose. Known beryllium plates, originating either from rolled sheet material or from sintered granular material, however, have insufficient plastic deformability for sealing such a surved window, while maintaining proper vacuumtightness. According to the invention, a beryllium plate is heated to a temperature of, for example, approximately 600°C so as to obtain the necessary deformation. During the heating, the desired shape is impressed on the plate, for example, by pressing it about a cylindrical mould. If desired, the deformation can be realized in a number of steps. This is advantageous, for example, if the plate is to be bent through more than 180° like in the described embodiment, or if the plate is to be bent in two directions. A window plate which has been bent through more than 180° offers the advantage that a slot can be covered thereby over at least 180°, with the result that the radial boundaries of the window opening impose no restriction whatsoever as regards the measuring range, that is to say the angle under which measuring takes place. A window opening of exactly 180° offers the practical advantage that the radial boundaries of the window are situated in the same plane as the specimen support face. It was found that a beryllium plate, regardless of the fact whether it originates from sheet material or from sintered material, can be plastically deformed to a much greater extent, also after cooling, after it has been heated to approximately the said temperature. Using such an annealed and deformed beryllium plate, having a thickness of, for example, 0.1 to 0.5 mm, the slot 17 is closed in a vacuumtight manner. To this end, the plate is connected to the housing at the area of the window wall 19, for example, by means of a suitable glue, or by soldering or diffusion. Measurements have revealed that a specimen holder thus sealed has a helium gas leakage of less than $10^{-10}$ torr liters per second. This means that the gas pressure in the specimen holder increases at the most to approximately $5 \times 10^{-5}$ torr during a analysis lasting, for example, 2 hours. The radiation loss in the beryllium window is amply compensated for by the gain due to the very low gas pressure about the specimen. A further substantial advantage of the specimen holder according to the invention is the fact that, due to the rotation symmetry, the X-ray beam is absorbed to the same extent everywhere, so that local absorption corrections can be dispensed with.

For specimens in the form of plates and the like an adapted support table can be readily constructed. For plate-shaped and conical specimens, the support face can be recessed so as to be adapted to the dimension of the specimen. The specimen holder can then remain unmodified.

FIG. 4 shows a preferred embodiment of a device for evacuating a specimen holder according to the invention. This device comprises a housing having a bottom portion 20 which is provided with an evacuation duct 21 which can be closed by a valve 22 which is not shown in detail. A removable upper portion 23 is provided on the bottom portion. In one or more recesses 24 and 0-ring can be provided for the vacuumtight sealing of a space 25. In the space 25 the specimen holder 1 is mounted, the flange 3 being directed towards the bottom portion. The lid 11 of the specimen holder can be fixed by means of a pin 26. To this end, the lid is provided with a recess 27 accommodating a clamping device 28. The clamping device 28 is constructed such that it is readily released after the lid 11 has been tightened (in this case by means of the thread 12). A sealing 0-ring can also be provided in one or more recesses 29.

After the evacuation of the specimen holder, the lid is closed and air can be admitted into the space 25. The upper portion can subsequently be removed and the specimen holder can be pushed out of the space 25 by means of the pin 26. The holder, thus provided with a specimen and evacuated, can then be arranged in the diffraction apparatus. No further steps need then be taken to prevent ingress of air. It is not objectionable either to prepare the specimen holder already some time before the measuring process commences.

What is claimed is:

1. A holder for an X-ray diffraction specimen which is to be fixed in a space to be conditioned comprising an evacuable housing that is provided with an external jacket, an external abutment face, a removable support table occupying a fixed position with respect to the said abutment face, said support table receiving said specimen, and with a radiation window preferably of beryllium, said window extending at least over a portion of said jacket about said specimen table.

2. A specimen holder as in claim 1, wherein said beryllium window is made of beryllium sheet material which has been annealed to approximately 600°C.

3. A specimen holder as in claim 1, wherein said window extends over an arc of at least 180°.

4. A specimen holder as in claim 1, wherein said support table has a support face which is adapted to the shape of said specimen.

5. An X-ray diffraction apparatus provided with a holder for an X-ray diffraction specimen which is to be fixed in a space to be conditioned comprising an evacuable housing that is provided with an external jacket, an external abutment face, a removable support table occupying a fixed position with respect to the said abutment face, said support table receiving said specimen, and with a radiation window preferably of beryllium, said window extending at least over a portion of said jacket about said specimen table; said apparatus further comprising a goniometer having an abutment face for accommodating said specimen holder in a measuring position.

* * * * *